(12) United States Patent
Bao et al.

(10) Patent No.: US 10,308,674 B2
(45) Date of Patent: Jun. 4, 2019

(54) PROCESS FOR PREPARING HIGH-PURITY L-ARABINOSE BY USING ARABIC GUM AS RAW MATERIAL

(71) Applicant: ZHEJIANG UNIVERSITY, Hangzhou, Zhejiang Province (CN)

(72) Inventors: Zongbi Bao, Hangzhou (CN); Minhui Huang, Hangzhou (CN); Zhiguo Zhang, Hangzhou (CN); Qiwei Yang, Hangzhou (CN); Baogen Su, Hangzhou (CN); Huabin Xing, Hangzhou (CN); Qilong Ren, Hangzhou (CN); Yiwen Yang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/550,655

(22) PCT Filed: May 7, 2015

(86) PCT No.: PCT/CN2015/078439
§ 371 (c)(1),
(2) Date: Aug. 11, 2017

(87) PCT Pub. No.: WO2016/149993
PCT Pub. Date: Sep. 29, 2016

(65) Prior Publication Data
US 2018/0030077 A1 Feb. 1, 2018

(30) Foreign Application Priority Data
Mar. 24, 2015 (CN) .......................... 2015 1 0130975

(51) Int. Cl.
*C07H 3/02* (2006.01)
*C07H 1/08* (2006.01)
(52) U.S. Cl.
CPC ................. *C07H 3/02* (2013.01); *C07H 1/08* (2013.01)

(58) Field of Classification Search
CPC .................................... C07H 3/02; C07H 1/08
USPC .......................... 435/105; 127/46.3; 536/128
See application file for complete search history.

(56) References Cited

U.S. PATENT DOCUMENTS 3,718,560 A * 2/1973 Sugiyama et al. ..... B01D 61/44
127/46.1
6,506,897 B1 1/2003 Antila et al.

FOREIGN PATENT DOCUMENTS

| CN | 101475607 A | | 7/2009 |
| CN | 102146102 | * | 8/2011 |
| CN | 102146102 A | | 8/2011 |
| CN | 102634612 A | | 8/2012 |
| GB | 2407573 A | | 5/2005 |

OTHER PUBLICATIONS

Anderson et al. Preparation of/-Arabinose from Mesquite Gum. Industrial and Engineering Chemistry vol. 17, No. 12. p. 1257-1258, Dec. 1925. (Year: 1925).*

* cited by examiner

*Primary Examiner* — Yih-Horng Shiao
(74) *Attorney, Agent, or Firm* — Jiwen Chen

(57) ABSTRACT

The present invention discloses a process for preparing L-arabinose from Gum Arabic comprising the steps of catalytical hydrolysis of L-arabinose from gum arabic followed by the purification steps including neutralization using alkali, adsorption bleaching, electrodialysis desalination, adsorption separation of impurities and crystallization, with the absolute purity of L-arabinose up to 98% and the recovery as high as 25%~29% of material weight. The disclosed process has such advantages as low cost, environmental-friendliness and simple operation, showing promising in industrial production.

7 Claims, 1 Drawing Sheet ical stage application of PCT Application No. PCT/CN2015/078439under 35 U.S.C. 371, filed May 7, 2015 in Chinese, claiming priority of Chinese Application No. 201510130975.0, filed Mar. 24, 2015, all of which are hereby incorporated by reference.

TECHNICAL FIELD

The present invention is related to the chemical engineering technology field, more specifically, a process for preparing high-purity L-arabinose from gum arabic as raw material. In practical terms, extraction and separation of high-purity L-Arabinose from gum arabic with the purification steps including hydrolysis reaction, neutralization, decolorization, adsorption and crystallization were reported.

BACKGROUND OF THE INVENTION

As a novel functional monosaccharide, L-arabinose is one type of important pharmaceutical intermediates, which is widely used in the synthesis of anticancer, antiviral and cardiovascular medicines such as cytarabine and L-ribose. It can also be used in biochemistry for preparation of culture medium and spices and so on. In addition, it has been discovered in recent year that L-arabinose has an excellent property of inhibiting the increase of glucose concentration in serum by inhibiting sucrose absorption noncompetitively. Thus it can prevent and treat obesity and hyperglycemia, showing a great market potential in weight loss and control of diabetes. L-arabinose has been approved as health food supplements by Food and Drug Administration (FDA) and The Japanese Ministry of Health, and it is also regarded as anti-obesity agents and nonprescription drugs by American Medical Association. So L-arabinose has wide prospect in medicine and food industries.

In nature, L-arabinose exists in fruit purees, hemicellulose, and pectate in the form of polysaccharide araban, L-araboxylan, L-arabinogalactan. Nowadays, the main industrial process for L-arabinose production still relies on extraction and purification using natural gum arabic as feedstock. Prior to the present invention, as introduced in relevant literatures, there are following methods for preparing L-arabinose from gum arabic.

The patent publication with the publication number of CN102146102A describes a method of preparing L-arabinose and D-galactose through hydrolysis of gum arabic with acid, then neutralization with aqueous alkali followed by evaporation. The mixture is then converted to the corresponding acetone acetals by ketone. It is selectively extracted with alcohol and finally deacetalize to obtain L-arabinose and D-galactose, with the yield as high as 15%~24% of material weight. Though L-arabinose and D-galactose can be obtained simultaneously, the process requires relatively large amounts of organic solvents and pollutes environment seriously.

It is not environmentally friendly, moreover, product purity is still far below standard. S. Mukher Jee and A. N. S Shrivastava used arabic Sundra gum as the raw material to obtain L-arabinose, D-galactose and rhamnose by means of hydrolysis followed by column chromatography with a large amount of half-saturated butanol aqueous solution (*J Sci. Ind. Research* India, 1956, 168, 566-7).

The patent publication with the publication number of CN1373135A describes a method of extraction of L-arabinose from Gum Arabic by chromatographic separation on two columns. Gum arabic is hydrolyzed with a mineral acid solution to yield the mixed solution followed by neutralization with alkali, which was concentrated and extracted with alcohol and then precipitated by quadruple amount of acetic acid. L-arabinose can be obtained further by chromatographic separation using n-butanol, ethyl acetate, iso-butanol, acetic acid as eluents. The purity of L-arabinose is 96%~99.5% and the yield is 16%~18%.

Patent EP0115068 describes a process for the production of L-arabinose from arabic PYCNANTHA gum. The process includes hydrolyzing gum with acids followed by neutralizing with IR-4B(OH) anion resin, and extracting with ethanol. L-arabinose and its derivatives can be obtained by column chromatography with a large amount of half-saturated ethyl acetate solution.

In summary, all forementioned purification methods require a great amount of organic solvents, resulting in large energy consumption and high cost. There are still some difficulties for these processes to be adopted for practical industrial production.

The patent publication with the publication number of CN102146102A proposes a different method for L-arabinose production. The gum arabic was firstly decomposed by enzyme, which is produced from a highly selective strain of *Fusarium* sp. The degradation mixture was then purified by traditional separation methods. The high-purity L-arabinose can be obtained with the recovery as 18% of material weight. The advantages of this method include mild reaction conditions and low dissipation of equipment. However, the process is still difficult to be industrialized because of inefficient hydrolysis and rigid operation conditions.

SUMMARY OF THE INVENTION

The present invention provides a method for preparing L-arabinose from gum arabic, with the absolute purity of L-arabinose up to 98% and the recovery as high as 25%~29% of material weight. The process have advantages over the other methods in terms of low cost, environmental-friendliness, and simple operation, showing very promising in the industrial application.

A method of preparing L-arabinose from gum arabic comprises the steps of:
(1) Hydrolysis: dissolving gum arabic followed by adding mineral acid, with controlled pH value of the solution at 0.2~1 and temperature at 70° C. to 100° C.; then neutralizing the hydrolysate with alkali aqueous solution to pH about 4~7.

The preferred alkali aqueous solution could be sodium hydroxide, potassium hydroxide, sodium carbonate, or potassium carbonate or the mixture of thereof, and the molar concentration is 10~20 mol/L. Alkali aqueous solution is the more preferred choice with the molar concentration of 15 mol/L, which is cheap and widely used in industrial production.

The preferred mineral acid is sulfuric acid, hydrochloric acid, phosphoric acid or a mixture of the two. The molar concentration of $H^+$ is 1~6 mol/L.

The preferred hydrolysis time is 1~5 hours, and the optimal time is 1~3 hours. It is not suitable to react for a long time, to avoid producing other monosaccharides and to facilitate subsequent separation.

Increasing the solid-liquid ratio will slow the hydrolysis rate. Besides, as increase of the concentrations of L-arabinose and other monosaccharides, it will become more difficult to conduct the subsequent separation and purification process. If the solid-liquid ratio is too small, the hydrolysate containing L-arabinose and other mono-saccharides will be very dilute. It requires more energy and time to concentrate the hydrolysate. So the preferred solid-liquid ratio is 1 kg: (8~12) L.

The more preferable hydrolysis conditions in Step (1) are suggested as follows: reaction for 1~2 hours at 90~100° C. with 1~2 mol/L $H_2SO_4$ and solid-to-liquid ratio of 1:10 (m/V).

For gum arabic's insolubilization in cold water, the particle size needs to be reduced by crushing. Dissolving the particle with hot water, followed by adding acid solution, to improve thermal efficiency and shorten hydrolysis time.

(2) Decoloration: feeding the hydrolysis of Step (1) into a fixed bed equipped with adsorbent A continuously, collecting the effluent.

The preferred adsorbent A is granular activated carbon, non-polar macroporous polystyrene adsorption resin, weak polar macroporous polystyrene adsorption resin, non-polar macroporous acrylic adsorption resin, weak polar macroporous acrylic adsorption resin, non-polar gel-type polystyrene adsorption resin, weak polar gel-type polystyrene adsorption resin, weak polar gel-type polystyrene acid adsorption resin, non-polar gel-type acrylic adsorption resin and weak polar gel-type acrylic adsorption resin.

The adsorbent shows better selectivity in removing pigment effectively, and the adsorption rate is quite fast. The recovery of the target L-arabinose and the discoloration rate are all above 95%. Additionally, the above adsorbent has stable physicochemical properties and high mechanical strength. As well, it is easy to be regenerated and has good cycle property.

An optimum is granular activated carbon, non-polar macroporous polystyrene adsorption resin or non-polar macroporous acrylic adsorption resin. The size of the activated carbon particles is 200~400 mesh.

The volume of the hydrolysate is 2~12 times the volume of the fixed bed.

The preferred decolorization conditions: the temperature range is 20~40° C., flow rate is 0.5~3 bed volume/hour.

Decoloring temperature should not be too high, or the feed rate should not be too high, otherwise the decolorization ability is poor.

The optimal decolorization conditions: the temperature range is 20~30° C., flow rate is 0.8~1.5 bed volume/hour.

(3) Desalination: handling the decolored solution with microporous membrane of the drainage, then desalinating the liquor with electroosmosis.

The process of the electrodialysis desalination comprises the steps of:

Taking the liquor and pure water as concentrated and dilute phase, and $Na_2SO_4$ as polar water, the liquor, and pure water and polar water are cycled in the instrument. Desalinating was performed for 2~5 hours under constant voltage and velocity.

The aperture of the microporous membrane of the drainage is 0.45 μm.

The concentration of $Na_2SO_4$ should not be too high in case it corrodes the equipment. The amount of pure water used get larger, the efficiency of desalination is higher. But it also has a large amount of wastewater and it requires more energy for recycle. So the amount of water should not be too large. The preferred mass concentration of $Na_2SO_4$ is 3%~8% and the preferred volume ratio of polar water, the liquor, and pure water is 0.25:1:1~3.

The preferred desalination conditions: operating voltage is 20~30 V, the liquid flow rate is 10~30 L/hour.

This way of desalination has merits including high filtering efficiency, large treatment quantity, low consumption of acid and alkali, small amount of wastewater, and controlled conditions. The equipment also possesses structure compact, elegant appearance and less occupied area. This method outperforms traditional ion exchange and reverse osmosis desalting process significantly.

The optimal desalination conditions:

Handling the decolored solution of Step (2) with microporous membrane of 0.45 μm of the drainage, then desalinating the liquor with electroosmosis at 20 L/hour under constant voltage of 25V for 2.5 hours, with the liquor, and pure water and polar water cycling in a concentrated solution, a diluted solution room and an electrode chamber of the instrument. The mass concentration of $Na_2SO_4$ is 3%~8% and the preferred volume ratio of polar water, the liquor, and pure water is 0.25:1:1~3.

(4) Adsorption separation: adding the liquor of Step (3) to fixed bed equipped with adsorbent B continuously, collecting the effluent. Supersaturated syrup can be obtained by concentrating under reduced pressure at 45~60° C.

The preferred adsorbent B is non-polar macroporous polystyrene adsorption resin, non-polar macroporous acrylic adsorption resin, non-polar gel-type polystyrene acid adsorption resin, non-polar gel-type acrylic a adsorption resin, granular activated carbon, silica gel bonded with C18 or C30.

The adsorbent has better selectivity of L-arabinose and other monosaccharides, large adsorption capacity. The recovery of the L-arabinose is above 85%. Additionally, the above adsorbent has high mechanical strength and is easy to be regenerated.

An optimum adsorbent B is granular activated carbon, non-polar macroporous polystyrene adsorption resin or non-polar macroporous acrylic resin.

The preferred solid concentration of liquor (desalination liquid) is 75 mg/mL~120 mg/mL, 5~8 BV of desalination liquid is added with flow of 0.5~1.5 BV/hour, and then the effluent can be collected.

An optimum volume and flow velocity are 6~7 BV and 0.5~1.5 BV/hour, respectively.

The water content of syrup obtained by concentrating under reduced pressure of Step (4) is 60%~200%.

(5) Crystallization: crystallizing and drying the supersaturated syrup of Step (4), obtaining the white crystallization L-arabinose.

The process of the crystallization of Step (5) comprises the steps of:

Dissolving the supersaturated syrup of Step (4) in alcohol, reducing the temperature to ambient temperature, inducing crystallization by adding some L-arabinose, filtering after crystallizing of 24~72 hours. Then the pure L-arabinose was obtained with purity up to 98% after drying in a vacuum oven at 50~60° C.

The alcohol is methanol or ethanol, the ratio of volume and the supersaturated syrup is 6~10:1 (L/kg).

The cooling rate is 0.2~3° C./min, crystallization temperature range is −5~10° C.

The thermal dissolution process comprises the steps of: dissolving the supersaturated syrup in 70%~90% methanol solution or ethanol solution, with the ratio of solution and syrup is 1:6~10, heating refluxing for 1~3 hours. The preferred alcohol solution is 70%~80% of ethanol solution, the volume ratio is 1:7~8. More preferably, after the obtained solution is naturally cooled, inducing crystallization by adding some L-arabinose for crystallizing for 24~72 hours The optimum crystalline condition is 0~5° C. for 48~56 hours.

The methodology of the recovery and purity in the present invention are shown as followed:

Recovery rate=mass of L-arabinose in solution after handling/mass of L-arabinose in solution before handling Purity=mass of L-arabinose in processed solution/total mass of solid in processed solution.

Term's meaning in the present invention is shown as followed:

The solution with solid content of 75-120 mg/mL means that there are 75~120 mg solid in the solution after being concentrating to constant quality. Due to complex composition, there are some insoluble substances. And the total mass is the whole weight of system, including the weight of suspension or precipitation.

BV: bed volume, the volume of activated carbon loading in the fixed bed in Step (2) and Step (4).

BV/h: the bed volume number of mobile phase feeding into the fixed bed per hour.

The process of the present invention is environmental-friendly because cost-efficient gum arabic with the highest amount of L-arabinose was used as a raw material and many highly efficient separation methods are combined in the process. L-arabinose hydrolysate can be obtained after hydrolyzing gum arabic with mineral acid. Pigment is adsorbed selectively by activated carbon. The liquor from adsorption step is desalinated followed by further separation and purification such as recrystallization. L-arabinose with purity up to 98% can be obtained after the integrated process, which is easy to realize in the industrial scale.

Compared with existing techniques, the technical solution of the invention has such advantages as few wastes, short process, and high L-arabinose yield, showing great potential in the industrial application with significant economic value.

DETAILED DESCRIPTION OF THE INVENTION

Figure 1:
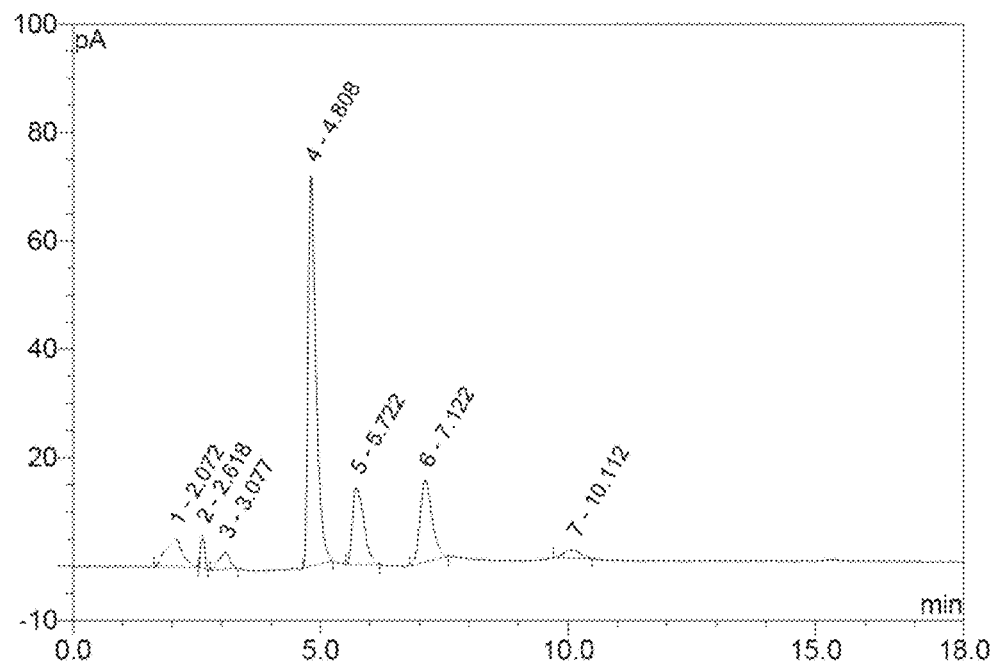
FIG. 1 HPLC chromatogram of products in embodiment 1 of the present invention

The present invention is described in reference to the following specific embodiments, basing on the preparation methods and test results of high-purity L-arabinose.

Embodiment 1

(1) Hydrolysis: 350 mL deionized water was added in a 1000 mL three-necked, round-bottomed flask, heating with oil bath to 80° C., and about 50 g of gum arabic was added with rapid magnetic stirring (speed=300~400 rpm) until it dissolves, and continue to heat to 90° C. Then, 150 mL preheated sulfuric acid solution (1 mol/L of $H_2SO_4$ was prepared by pipetting 50 mL 50% oleum followed by diluting with water to 1 L) was added to the resulting mixture, accompanying with temperature reducing to 74~78° C. Herein, the concentration of sulfuric acid in solution was 0.3 mol/L (pH=0.51). The reaction was kept for 1 hour before stopping stirring and heating, followed by transferring hydrolysate to 2 L sealed conical flask, and the reaction was terminated in a cold bath quickly. 537 mL of liquor was obtained, which contained 23.42 g arabinose with purity as 51%, and then neutralize to pH=7 with 15M NaOH.

(2) Decoloration: The liquid was delivered to the fixed bed equipped with 200~400 mesh activated carbon (high: 30.0 cm, inner diameter: 1.5 cm), which was packed moistly and pressed with high flow-rate of pure water. The bed volume of the activated carbon column (BV) was 53 mL and the flow rate of feeding solution was 1.32 mL/min (1.5 BV/h). 506 mL effluent was collected containing 23.42 g arabinose, and recovery of this phase was up to 90%.

(3) Desalination: Decoloring solution was handled with 0.45 μm microporous membrane of the drainage before adding electrodialysis with 5 wt % $Na_2SO_4$ as polar water. The electrodialysis conditions: voltage is 25 V, the flow of material was 20 L/h. The volume ratio of the polar water, pre-processed solution and pure water is 0.25:1:1. The electrical conductivity of desalting chamber was decreased from 11.2 mS/cm to 340 μS/cm after desalination for 2.5 hours. 481 mL liquor was collected containing 19.51 g arabinose, with purity up to 60%. And the recovery of this step was about 92%.

(4) Adsorption separation: The liquid was delivered to the 200~400 mesh activated carbon fixed bed equipped with to activated carbon (high: 25.0 cm, inner diameter: 1.0 cm), which was packed moistly and pressed with high flow-rate of pure water. The bed volume of the activated carbon column (BV) was 20 mL and the flow rate of feeding solution was 0.5 mL/min (1.5 BV/h). 371 ml solution was collected with effluent of 4~11 BV containing 16.71 g arabinose with purity up to 88%, the recovery of this step was about 85%.

Figure 2:
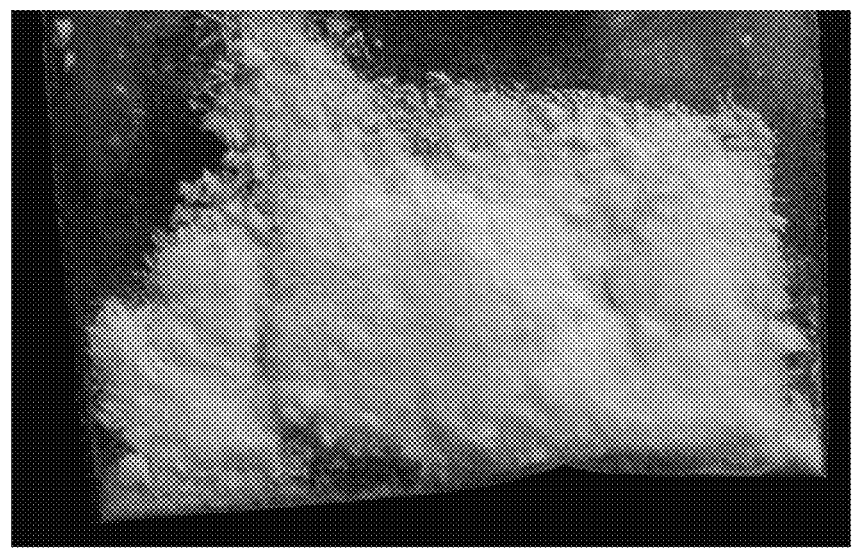
FIG. 2 Physical photo of pure L-arabinose in embodiment 1 of the present invention

(5) Crystallization: effluent was distillated reduced pressure to syrup before adding 80% ethanol solution, and with solid to liquid ratio was 1:8. The solution was refluxed for 3 hours in a water bath of 92° C., and then cooled down to room temperature. The solution stayed in the refrigerator of 5° C. for 56 hours. The crystal was filtered and washed with little absolute ethanol. The filtrate was cycled to Step (4) after solvents recovering. The product was dried in a vacuum oven at 25° C. for 4 hours. 14.51 g L-arabinose can be obtained with purity as 98.5%. The recovery of L-arabinose in whole process was 62% basing on the mass of L-arabinose in hydrolysate, or 29% of the mass of gum arabic. The HPLC chromatogram of the obtained product is shown in FIG. 1 and the photo of the physical product is shown in FIG. 2.

Embodiment 2

(1) Hydrolysis: 450 mL deionized water was added in a 1000 mL three-necked, round-bottomed flask, heating with oil bath to 80° C., and about 40 g of gum arabic was added with rapid magnetic stirring (speed=300~400 rpm) until it dissolves, and continued to heat to 90° C. Then, 50 mL preheated sulfuric acid solution (1 mol/L of $H_2SO_4$ was prepared by pipetting 50 mL 50% oleum followed by diluting with water to 1 L) was added to the resulting mixture, accompanying with temperature reducing to 74~78° C. Herein, the concentration of sulfuric acid in solution was 0.1 mol/L (pH=0.70). The reaction was kept for 3 hours before stopping stirring and heating, followed by transferring hydrolysate to 2 L sealed conical flask, and the reaction was terminated in a cold bath quickly. 523 mL liquor was obtained, which contained 19.23 g arabinose with purity as 49%, and then neutralize to pH=7 with 15M NaOH.

(2) Decoloration: The liquid was delivered to the fixed bed equipped with 200~400 mesh non-polar macroporous polystyrene resin (high: 25.0 cm, inner diameter: 1.5 cm), which was packed moistly and pressed with high flow-rate of pure water. The bed volume of the activated carbon column (BV) was 44 mL and the flow rate of feeding solution was 0.75 mL/min (1 BV/hour). 502 mL effluent was collected containing 17.56 g arabinose, and recovery of this phase was up to 91%.

(3) Desalination: Decoloring solution was handled with 0.45 μm microporous membrane of the drainage before adding electrodialysis with 5 wt % $Na_2SO_4$ as polar water. The electrodialysis conditions: voltage is 25 V, the flow of material was 15 L/h. The electrical conductivity of desalting chamber was decreased from 10.05 mS/cm to 278 μS/cm after desalination for 2 hours. 475 mL liquor was collected containing 15.94 g arabinose, with purity up to 62%. The recovery of this step was about 91%.

(4) Adsorption separation: The liquid was delivered to the 200~400 mesh activated carbon fixed bed equipped with to activated carbon (high: 25.0 cm, inner diameter: 1.0 cm), which was packed moistly and pressed under high speed pure water flow. The bed volume of the activated carbon column (BV) was 20 mL and the flow rate was 0.4 mL/min (1.2 BV/h). 354 ml solution was collected with effluent of 3~9 BV containing 13.75 g arabinose with purity up to 88%, the recovery of this step was about 86%.

(5) Crystallization: effluent was distilled reduced pressure to syrup before adding 80% ethanol solution, and with solid to liquid ratio was 1:8. The solution was refluxed for 3 hours in a water bath of 92° C., and then cooled down to room temperature. The solution stayed in the refrigerator of 5° C. for 56 hours. The crystal was filtered and washed with little absolute ethanol. The filtrate was cycled to Step (4) after solvents recovering. The product was dried in a vacuum oven at 25° C. for 4 hours. 11.45 g L-arabinose can be obtained with purity as 98.2%. The recovery of L-arabinose in whole process was 60% basing on the mass of L-arabinose in hydrolysate, or 28% of the mass of gum arabic.

Measurement Methods of L-arabinose Concentration

The concentration of L-arabinose, D-galactose and L-rhamnose is measured by the following way in the above embodiment.

The analytical method of UHPLC is established by ultra performance liquid chromatograph of DIONEX D3000 and the detector is corona charged aerosol detection (CAD). Chromatographic column: GRACE Prevail Carbohydrate ES (250 mm×4.6 mm, 5 μm); the sample volume: 5 μL; mobile phase: acetonitrile-water (75:25); flow rate: 1 mL/min; column temperature: 30° C.

The concentration range of the monosaccharides:
L-arabinose: 0.5~4 g/L; D-galactose: 0.1~1 g/ L; L-rhamnose: 0.1~1.5 g/L The calibrated curve of the monosaccharides:
L-arabinose: $y=0.0036x^2+0.2665x$, $R^2=0.9991$; D-galactose: $y=0.0017x^2+0.1329x$, $R^2=0.9998$; L-rhamnose: $y=0.0014x^2+0.0331x$, $R^2=0.9995$. X—peak area, y—concentration.

The above embodiment is optimization of the present invention. To traditional technician, the improvement and polish also belong to the scope of protection of the invention, which base on the technology principle of the present invention.

The invention claimed is:

1. A process for preparing high-purity L-arabinose from gum arabic, the process comprising the following steps:

(1) adding dissolved gum arabic into an inorganic acid to form a mixed solution, controlling pH value of the solution at 0.2~1, undertaking hydrolysis reaction at the temperature of 70~100° C., after the reaction, neutralizing the hydrolysate by adding an alkali aqueous solution to reach pH of about 4~7 and obtaining the neutralized hydrolysate containing L-arabinose;

(2) adding the hydrolysate of step (1) to a fixed bed equipped with an adsorbent A continuously, collecting an effluent that passes through the adsorbent A to form a decolored solution;

(3) passing the decolored solution of step (2) through a microporous membrane of a drainage to obtain a pretreatment solution, then desalinating the pretreatment solution by electrodialysis to obtain a desalination solution;

(4) passing the desalination solution of step (3) through a fixed bed equipped with an adsorbent B continuously under room temperature, collecting an effluent that passes through the adsorbent B, obtaining a supersaturated syrup by concentrating the effluent that passes through the adsorbent B under reduced pressure at 45~60° C.; and (5) crystallizing the supersaturated syrup and obtaining white powder of L-arabinose after drying;

wherein the adsorbent A is one of granular activated carbon, non-polar macroporous polystyrene adsorption resin, weak polar macroporous polystyrene adsorption resin, non-polar macroporous acrylic adsorption resin, weak polar macroporous acrylic adsorption resin, non-polar gel-type polystyrene adsorption resin, weak polar gel-type polystyrene adsorption resin, weak polar gel-type polystyrene acid adsorption resin, non-polar gel-type acrylic adsorption resin and weak polar gel-type acrylic adsorption resin;

wherein the process of the electrodialysis consists of the steps of: circulating the pretreatment solution in concentrated solution chamber and pure water in diluted solution chamber of an electrodialysis instrument respectively through electrode chamber that contains $Na_2SO_4$ as polar water and desalinating for 2~5 hours under constant voltage and velocity;

wherein the adsorbent B is one of non-polar macroporous polystyrene adsorption resin, non-polar macroporous acrylic adsorption resin, non-polar gel-type polystyrene acid adsorption resin, non-polar gel-type acrylic adsorption resin, granular activated carbon, and silica gel bonded with C18 or C30; and wherein the process of the crystallization comprises the steps of:

dissolving the supersaturated syrup of step (4) in alcohol, cooling the temperature to ambient temperature, inducing crystallization by adding some L-arabinose, filtering after crystallizing for 24~72 hours, and obtaining pure L-arabinose with purity of 98% or higher after drying in a vacuum oven at 50~60° C.;

the alcohol is methanol or ethanol, the ratio of alcohol volume to the supersaturated syrup by weight is (6~10) L: 1 kg, the cooling rate is 0.2~3° C./min and crystallization temperature range is −5~10° C.

2. The process for preparing high-purity L-arabinose from gum arabic according to claim 1, wherein the inorganic acid is sulfuric acid, hydrochloric acid, phosphoric acid or mixture of two thereof and molar concentration of $H^+$ is 1~6 mol/L.

3. The process for preparing high-purity L-arabinose from gum arabic according to claim 1, wherein the hydrolysis time is 1~5 hours.

4. The process for preparing high-purity L-arabinose from gum arabic according to claim 1, wherein decolorization temperature of step (2) is 20~55° C. and flow rate is 0.5~3 bed volume/hour.

5. The process for preparing high-purity L-arabinose from gum arabic according to claim 1, wherein the mass concentration of $Na_2SO_4$ is 3% ~8% and the volume ratio of the pretreatment solution and pure water is 1: 1~3.

6. The process for preparing high-purity L-arabinose from gum arabic according to claim 1, wherein the desalination conditions are as follows: operating voltage is 20~30 V and the solutions flow rate is 10~30 L/hours.

7. A process for preparing high-purity L-arabinose from gum arabic, the process comprising the following steps:
  (1) adding dissolved gum arabic into an inorganic acid to form a mixed solution, controlling pH value of the solution at 0.2~1, undertaking hydrolysis reaction at the temperature of 70~100° C., after the reaction, neutralizing the hydrolysate by adding an alkali aqueous solution to reach pH of about 4~7 and obtaining the neutralized hydrolysate containing L-arabinose;
  (2) adding the hydrolysate of step (1) to a fixed bed equipped with an adsorbent A continuously, collecting an effluent that passes through the adsorbent A to form a decolored solution;
  (3) passing the decolored solution of step (2) through a microporous membrane of a drainage to obtain a pretreatment solution, then desalinating the pretreatment solution by electrodialysis to obtain a desalination solution;
  (4) passing the desalination solution of step (3) through a fixed bed equipped with an adsorbent B continuously under room temperature, collecting an effluent that passes through the adsorbent B, obtaining a supersaturated syrup by concentrating the effluent that passes through the adsorbent B under reduced pressure at 45~60° C.; and
  (5) crystallizing the supersaturated syrup and obtaining white powder of L-arabinose after drying;
  wherein the adsorbent A is one of granular activated carbon, non-polar macroporous polystyrene adsorption resin, weak polar macroporous polystyrene adsorption resin, non-polar macroporous acrylic adsorption resin, weak polar macroporous acrylic adsorption resin, non-polar gel-type polystyrene adsorption resin, weak polar gel-type polystyrene adsorption resin, weak polar gel-type polystyrene acid adsorption resin, non-polar gel-type acrylic adsorption resin and weak polar gel-type acrylic adsorption resin;
  wherein the process of the electrodialysis consists of the steps of: circulating the pretreatment solution in concentrated solution chamber and pure water in diluted solution chamber of an electrodialysis instrument respectively through electrode chamber that contains $Na_2SO_4$ as polar water and desalinating for 2~5 hours under constant voltage and velocity;
  wherein the adsorbent B is one of non-polar macroporous polystyrene adsorption resin, non-polar macroporous acrylic adsorption resin, non-polar gel-type polystyrene acid adsorption resin, non-polar gel-type acrylic adsorption resin, granular activated carbon, and silica gel bonded with C18 or C30;
  wherein the process of the crystallization comprises the steps of:
  dissolving the supersaturated syrup of step (4) in alcohol, cooling the temperature to ambient temperature, inducing crystallization by adding some L-arabinose, filtering after crystallizing for 24~72 hours, and obtaining pure L-arabinose with purity of 98% or higher after drying in a vacuum oven at 50~60° C.;
  the alcohol is methanol or ethanol, the ratio of alcohol volume to the supersaturated syrup by weight is (6~10) L: 1 kg, the cooling rate is 0.2~3° C./min and crystallization temperature range is -5~10° C.;
  wherein the inorganic acid is sulfuric acid, hydrochloric acid, phosphoric acid or mixture of two thereof and molar concentration of $H^+$ is 1~6 mol/L;
  wherein the hydrolysis time is 1~5 hours;
  wherein decolorization temperature of step (2) is 20~55° C. and flow rate is 0.5~3 bed volume/hour;
  wherein the mass concentration of $Na_2SO_4$ is 3% -~8% and the volume ratio of the pretreatment solution and pure water is 1: 1~3; and
  wherein the desalination conditions are as follows: operating voltage is 20~30 V and the solutions flow rate is 10~30 L/hours.

* * * * *